United States Patent
Sangekar et al.

(10) Patent No.: US 6,632,455 B2
(45) Date of Patent: *Oct. 14, 2003

(54) MOLECULAR DISPERSION COMPOSITION WITH ENHANCED BIOAVAILABILITY

(75) Inventors: Surendra A. Sangekar, Union, NJ (US); Ping I. Lee, Radnor, PA (US); Amin A. Nomeir, Milford, NJ (US)

(73) Assignee: Schering Corporation, Kenilworth, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/215,603

(22) Filed: Dec. 17, 1998

(65) Prior Publication Data

US 2001/0016209 A1 Aug. 23, 2001

Related U.S. Application Data

(60) Provisional application No. 60/068,387, filed on Dec. 22, 1997.

(51) Int. Cl.[7] ............................. A61K 9/10; A61K 9/20; A61K 9/48; A61K 47/32
(52) U.S. Cl. ....................... 424/486; 514/960; 424/465; 424/452
(58) Field of Search ................................. 424/486, 469, 424/468, 457, 470, 452, 465; 514/960, 964–65

(56) References Cited

U.S. PATENT DOCUMENTS

| | | | |
|---|---|---|---|
| 4,764,378 A | * | 8/1988 | Keith et al. |
| 4,826,853 A | | 5/1989 | Piwinski et al. |
| 5,073,379 A | * | 12/1991 | Klimesch et al. |
| 5,089,496 A | | 2/1992 | Piwinski et al. |
| 5,151,423 A | | 9/1992 | Piwinski et al. |
| 5,393,890 A | | 2/1995 | Syoji et al. |
| 5,464,840 A | | 11/1995 | Ting et al. |
| 5,512,293 A | * | 4/1996 | Landrau et al. |
| 5,523,095 A | * | 6/1996 | Wilson et al. |
| 5,561,117 A | | 10/1996 | Wong et al. |
| 5,595,762 A | * | 1/1997 | Derrieu et al. |
| 5,661,152 A | | 8/1997 | Bishop et al. |
| 5,672,611 A | | 9/1997 | Doll et al. |
| 5,684,013 A | | 11/1997 | Afonso et al. |
| 5,696,121 A | | 12/1997 | Bishop et al. |
| 5,700,806 A | | 12/1997 | Doll et al. |
| 5,703,090 A | | 12/1997 | Afonso et al. |
| 5,712,280 A | | 1/1998 | Doll et al. |
| 5,714,609 A | | 2/1998 | Doll et al. |
| 5,719,148 A | | 2/1998 | Bishop et al. |
| 5,721,236 A | | 2/1998 | Bishop et al. |
| 5,728,703 A | | 3/1998 | Bishop et al. |
| 5,807,853 A | | 9/1998 | Bishop et al. |

(List continued on next page.)

FOREIGN PATENT DOCUMENTS

| | | |
|---|---|---|
| EP | 0 214 092 | 3/1987 |
| EP | 0270818 | 6/1988 |
| EP | 0 341 860 | 11/1989 |
| EP | 396083 | 11/1990 |
| EP | 0495484 | 7/1992 |
| GB | 1 560 406 | 2/1980 |
| WO | WO95/10515 | 4/1995 |
| WO | WO95/10516 | 4/1995 |
| WO | WO95/15949 | 6/1995 |
| WO | WO96/30018 | 10/1996 |
| WO | WO96/30362 | 10/1996 |
| WO | WO96/30363 | 10/1996 |
| WO | WO96/31477 | 10/1996 |
| WO | WO96/31478 | 10/1996 |
| WO | WO97/23478 | 7/1997 |
| WO | WO98/00113 | 1/1998 |
| WO | WO99/32118 | 7/1999 |

OTHER PUBLICATIONS

Bishop et al., The Journal of Biological Chemistry, vol. 270, No. 15, pp. 30611–30618 (1995).

Njoroge et al., Bioorganic & Medicinal Chemistry Leters, vol. 6, No.24, pp. 2977–2982 (1996).

Buhler, Volker, Kollidon, Polyvinylpyrrolidone for the Pharm. Industry, 2$^{nd}$ Edition, pp. 88–105; 169–177;245–271 (1993).

A.T. Florence and D. Attwood, "Physicochemical Principles of Pharmacy" MacMillan Press Ltd., Chapter 2.9, p. 41–45 (1988).

Patent Abstracts of Japan, vol. 096, No. 006, (1996).

Liu M. et al., Cancer Research, 58 (21) pp. 4947–4956, (1998).

*Primary Examiner*—Edward J. Webman
(74) *Attorney, Agent, or Firm*—Alan N. Kutzenco; Thomas D. Hoffman

(57) ABSTRACT

A molecular dispersion composition is disclosed. The molecular dispersion comprises a compound of the formula:

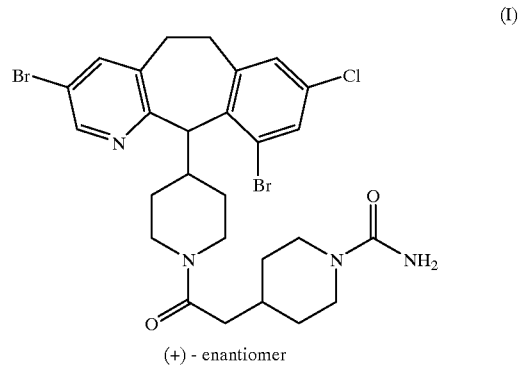

(I)

(+) - enantiomer molecularly dispersed in a polymer matrix. Also disclosed are solid dosage forms, e.g., tablets and capsules, containing these molecular dispersions.

3 Claims, No Drawings

U.S. PATENT DOCUMENTS

| | | |
|---|---|---|
| 5,834,472 A | 11/1998 | Sangekar et al. ........... 514/252 |
| 5,852,034 A | 12/1998 | Njoroge et al. |
| 5,858,411 A * | 1/1999 | Nakagami et al. |
| 5,861,395 A | 1/1999 | Taveras et al. |
| 5,874,442 A | 2/1999 | Doll et al. |
| 5,877,177 A | 3/1999 | Taveras |
| 5,925,639 A | 7/1999 | Doll et al. |
| 5,939,416 A | 8/1999 | Rane et al. |
| 5,945,429 A | 8/1999 | Taveras et al. |
| 5,958,890 A | 9/1999 | Rane et al. |
| 5,958,939 A | 9/1999 | Afonso et al. |
| 5,958,940 A | 9/1999 | Rane et al. |
| 5,965,570 A | 10/1999 | Cooper et al. |
| 5,972,381 A | 10/1999 | Sangekar et al. |
| 5,985,879 A | 11/1999 | Taveras et al. |
| 6,030,982 A | 2/2000 | Njoroge et al. |
| 6,040,305 A | 3/2000 | Taveras et al. |
| 6,071,907 A | 6/2000 | Njoroge et al. |

* cited by examiner

MOLECULAR DISPERSION COMPOSITION WITH ENHANCED BIOAVAILABILITY

This application claims the benefit of U.S. Provisional Application No. 60/068,387, filed Dec. 22, 1997.

BACKGROUND OF THE INVENTION

The present invention relates to compositions having enhanced or improved bioavailability for a novel tricyclic amide compound.

WO 97/23478, published Jul. 3, 1997, discloses tricyclic amides useful for inhibition of G-Protein function and for treatment of proliferative diseases. One particular compound (+)-4-[4-(8-chloro-3,10-dibromo-6,11-dihydro-5H-benzo[5,6cyclohepta[1,2-b]pyridin-11-yl)-1-piperidinyl]-2-oxoethyl]-1-piperidinecarboxamide (Compound I)

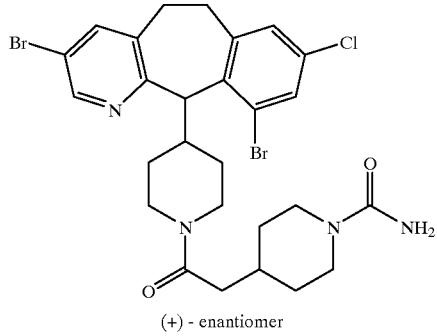

(+) - enantiomer was found to have potent activity for inhibiting the abnormal growth of cells, and for inhibiting farnesyl protein transferase.

WO 97/23478 discloses that examples of suitable compositions of this compound include solid compositions such as tablets and capsules.

In developing a solid dosage form, e.g. a tablet or capsule, it was observed that crystalline Compound I had very poor bioavailability, did not seem suitable for development as a tablet or capsule.

The oral bioavailability of active compounds can vary with the dosage form of the active compound. For example, it is known that solution dosages and suspensions generally give rise to higher bioavailability than capsules or tablets (see Pharmacokinetics Process and Mathematics, ACS Monograph 185, Chapter 5, page 57 (1986), and J. G. Nairn, Remington's Pharmaceutical Sciences, 18th edition (1990)). However, tablets and capsules are more convenient dosage forms, and it would be preferable to have a tablet or a capsule dosage form of an active compound that has comparable bioavailability as that of solution or suspension.

A formulation of compound I that provides enhanced bioavailability of the compound would be a welcome contribution to the art. A formulation of the above compound that can be manufactured in a tablet or capsule form that has greater bioavailability, or comparable to that of a suspension would also be a welcome contribution to the art. This invention provides these contributions to the art. Thus, this invention overcomes the problem of making active compounds that have a very-low bioavailability into more bioavailable form.

SUMMARY OF THE INVENTION

The present invention provides a pharmaceutical composition comprising:

a molecular dispersion, said molecular dispersion comprising a compound having the formula

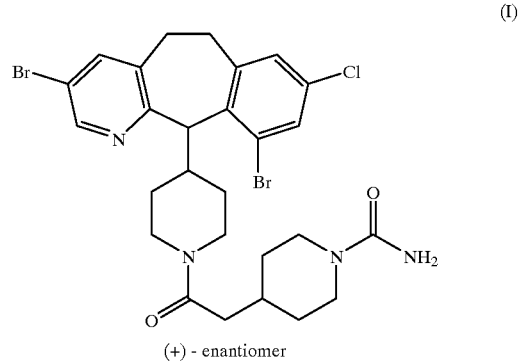

(+) - enantiomer molecularly dispersed in a polymer matrix.

This invention also provides solid dosage forms comprising the molecular dispersion described above. Solid dosage forms include tablets, capsules and chewable tablets. Known excipients can be blended with the molecular dispersion to provide the desired dosage form. For example, a capsule can contain the molecular dispersion blended with (a) a disintegrant and a lubricant, or (b) a disintegrant, a lubricant and a surfactant. A tablet can contain the molecular dispersion blended with at least one disintegrant, a lubricant, a surfactant, and a glidant. The chewable tablet can contain the molecular dispersion blended with a bulking agent, a lubricant, and if desired an additional sweetening agent (such as an artificial sweetener), and suitable flavors.

DETAILED DESCRIPTION OF THE INVENTION

The compound of Formula I is a tricyclic amide compound described in WO 97/23478, published Jul. 3, 1997.

Reference to the "compound of Formula I" also includes reference to the enantiomers of the compound.

As used herein, the term "molecularly dispersed" or "molecular dispersion" refers to a condition in which: (a) compound (I) is in a substantially amorphous form and is dispersed in a polymer matrix (also known as a "solid solution"), or (b) compound (I) is in crystalline form and is dispersed in a polymer matrix, the crystals being so fine, that they can not be detected by x-ray diffraction analysis.

As used herein, the term "substantially amorphous" refers to a condition in which greater than 90% of compound (I) is in amorphous form.

When the molecular dispersion is a dispersion of compound (I) in substantially amorphous form, such molecular dispersions may be prepared by dissolving the compound and a polymer in a suitable organic solvent, or mixture of organic solvents, and then removing the solvent to produce a molecular dispersion. The molecular dispersions formed in this manner are such that compound (I) is in substantially amorphous form, and homogeneously dispersed in the polymer matrix. Preferably, the polymer is a water soluble polymer. When water insoluble polymers are employed instead of water soluble polymers, the resulting molecular dispersions have enhanced bioavailability, but will exhibit a sustained release profile.

Alternatively, the molecular dispersions may be prepared by dissolving the compound of formula (I) in an organic solvent that will swell a polymer matrix instead of dissolving the polymer. The polymer matrix will absorb the active solution, rendering compound (I) in a fine crystalline or amorphous state dispersed throughout the matrix, upon subsequent evaporation of the solvent.

The preparation of solid solutions from soluble polymers is well known in the art—see, for example, page 173 in Kollidon—polyvinylpyrrolidone for the pharmaceutical industry by BASF. The preparation of solid solutions from insoluble polymeric matrices are also known in the art, and such preparations are similar to those for drug loading into crosslinked hydrogels—see for example, U.S. Pat. No. 4,624,848 and Lee, P. I., Kinetics of Drug Release from Hydrogel Matrices, Journal of Controlled Release, Vol. II, pages 277 to 288 (1985).

Suitable water soluble polymers for use as the polymer matrix include, but are not limited to: polyvinylpyrrolidone (Povidone); hydroxypropyl methylcellulose, hydroxypropyl-cellulose; polyethylene glycol; polyethylene oxide; gelatin; carbomer; carboxymethyl-cellulose; methyl cellulose; methacrylic acid copolymer; ammonio methacrylate copolymer; hydroxy ethyl cellulose; polyvinyl alcohol; cellulose acetate phthalate; hydroxypropyl methylcellulose phthalate; and polyvinyl alcohol phthalate.

Suitable water insoluble polymers for use as the polymer matrix include, but are not limited to: crospovidone; sodium starch glycolate; and croscarmellose.

Preferably, the polymer used for the polymeric matrix is selected from the group consisting of polyvinylpyrrolidone (Povidone), hydroxypropyl methylcellulose, hydroxypropyl-cellulose, and polyethylene glycol. Polyvinylpyrrolidone is particularly preferred. When a water isoluble polymer is employed, crospovidone is preferred.

All of the foregoing polymers are well known in the art.

Polyvinylpyrrolidone represents polymers of 1-vinyl-2-pyrrolidone. It is available commercially as Povidone or Kollidon having a weight average ranging from about 12,000 to about 150,000. Generally, the polyvinylpyrrolidone used has a weight average in the range of about 7000 to about 54,000, with about 28,000 to about 54,000 being preferred, and about 29,000 to about 44,000 being more preferred.

Crospovidone represents water insoluble synthetic crosslinked homopolymers of N-vinyl-2-pyrrolidone. Generally, the crospovidone has a particle size of about 20 $\mu$M to about 250 $\mu$M, and preferably about 50 $\mu$M to about 250 $\mu$M (see, for example, Kollidon, polyvinylpyrrolidone for the pharmaceutical industry, by BASF).

Preferably, the ratio of the compound of formula (I) to polymer is about 1:0.5 to about 1:4, more preferably about 1:1 to about 1:3, and most preferably, about 1:1.

When the molecular dispersions of the present invention are prepared by dissolving the compound of formula I and the polymer in an organic solvent or mixture of organic solvents, suitable organic solvents include, but are not limited to methylene chloride, methanol, ethanol, isopropanol, tetrahydrofuran, or mixtures thereof.

The solvent may be removed by conventional means: e.g., evaporating the solvent under a hood; use of a double drum dryer, or spray dryer or supercritical fluid extraction process.

The composition comprising the molecular dispersion can, optionally, further comprise excipients selected from the group consisting of: disintegrants, lubricants, surfactants, glidants, artificial sweeteners, bulking agents, colorants and one or more flavorants.

Generally the compound I ranges from 15 to 60% in the formulations (tablets, capsules, or powders).

Generally, the composition comprising the molecular dispersion can, optionally, further comprise: about 5 to about 40 wt % of one or more disintegrants, about 0.1 to about 1 wt % of one or more lubricants, about 3 to about 15 wt % of one or more surfactants, about 0.1 to about 5 wt % of one or more glidants, about 0.1 to about 1 wt % of one or more artificial sweeteners, about 25 to about 75 wt % of one or more bulking agents, about 0.1 to about 1 wt % of one or more colorants (coloring agents), and/or about 0.1 to about 1 wt % of one or more flavorants (flavoring agents).

Suitable disintegrants are selected from the group consisting of: croscarmellose sodium (a cross linked polymer of carboxymethylcellulose sodium, see NF XVII page 1922 (1990)), crospovidone, starch NF; polacrilin sodium or potassium and sodium starch glycolate. Preferably, the disintegrants are selected from croscarmellose sodium or crospovidone. Preferably, croscarmellose sodium is used as the disintegrant in compositions for capsules. Preferably, crospovidone is used as the disintegrant in compressible tablets. Those skilled in the art will appreciate that it is desirable for compressible tablets to disintegrate within 30 minutes; therefore, the disintegrant used preferably results in the disintegration of the tablet within 30 minutes. It has been found that disintegrants, such as croscarmellose sodium and crospovidone, used in amounts of less than 30 wt % did not produce tablets which disintegrated within 30 minutes. It is believed that significantly higher amounts of such disintegrants would result in a tablet that disintegrates within 30 minutes.

Suitable lubricants include talc, magnesium stearate, calcium stearate, stearic acid, hydrogenated vegetable oils and the like. Preferably, magnesium stearate is used.

Suitable surfactants include block copolymers of ethylene oxide and propylene oxide such as Pluronic® F-68 (Poloxamer 188), Pluronic® F87 (Poloxamer 237), Pluronic® F108 (Poloxamer 338), Pluronic® F127 (Poloxamer 407) and the like. Preferably, Pluronic® F-68 is used. According to BASF Corporation's Technical Bulletin (1995), Pluronic® is a registered tradename for block copolymers of ethylene oxide and propylene oxide represented by the chemical structure $HO(C_2H_4O)_a(C_3H_6O)_b(C_2H_4O)_aH$ wherein for: (a) Pluronic® F-68, a is 80 and b is 27; (b) Pluronic® F87, a is 64 and b is 37; (c) Pluronic® F108, a is 141 and b is 44; and Pluronic® F127, a is 101 and b is 56. The average molecular weights of these block copolymers are 8,400, 7,700, 14,600 and 12,600 for Pluronic F-68, Pluronic F-87, Pluronic F108 and Pluronic F127, respectively.

Suitable glidants include silicon dioxide, talc and the like. Preferably, silicon dioxide is used.

Suitable bulking agents include xylitol, mannitol, compressible sugars, lactose, and microcrystalline celluloses. Preferably, xylitol is used for chewable tablets.

Suitable artificial sweeteners include saccharin, cyclamates and aspartame.

If desired, known flavorants and known FD & C colorants can be added to the composition.

The composition comprising the molecular dispersion can be produced in solid dosage forms. Solid dosage forms include capsules (e.g., soft gelatin capsules and hard gelatin capsules) tablets (including, for example, coated tablets, gel coated tablets and enteric coated tablets), and chewable tablets. These dosage forms can be produced by methods well known in the art—see for example Lachman et al., The Theory and Practice of Industrial Pharmacy, 2nd Edition, Lea & Febiger, Philadelphia, pages 321–344 and pages 389–404 (1976).

For capsule dosage forms, the composition comprising the molecular dispersion generally further comprises disintegrants, lubricants, and, optionally, surfactants. Thus, a composition for use in capsules can comprise about 65 to about 90 wt % of the molecular dispersion, about 5 to about 20 wt % of one or more disintegrants, about 0.2 to about 1 wt % of one or more lubricants, about 1–3% of glidant and, optionally, about 3 to about 15 wt % of one or more surfactants.

For example, a composition for use in a capsule dosage form comprises: about 80 to about 85 wt % of the molecular dispersion, about 5 to about 10 wt % of one or more disintegrants, about 0.5 to about 1 wt % of one or more lubricants, about 0.5 to about 1.5% glident and about 3 to 10% of surfactant.

Another example of a composition for use in a capsule dosage form is a composition comprising about 70 to about 85 wt % of the molecular dispersion, about 5 to about 20 wt % of one or more disintegrants, about 0.3 to about 1 wt % of one or more lubricants, and about 5 to about 15 wt % of one or more surfactants and 1–3% glidant. In general, the compositions for capsule dosage forms contain the molecular dispersion, one disintegrant, one lubricant, one glident and optionally, one surfactant. Preferably, the disintegrant in the capsule compositions is croscarmellose sodium.

For a compressible tablet dosage form, the composition comprising the molecular dispersion generally further comprises disintegrants, lubricants, surfactants, and glidants. Thus, a composition for use in compressible tablets can comprise about 50 to about 75 wt % of the molecular dispersion, about 20 to about 45 wt % of one or more disintegrants, with about 28 to about 35 wt % of one or more disintegrants being preferred, about 0.2 to about 1 wt % of one or more lubricants, about 4 to about 10 wt % of one or more surfactants, and about 0.2 to about 0.6 wt % of one or more glidants. Preferably, the disintegrant is crospovidone. More preferably, the disintegrant is crospovidone in an amount of about 8 to about 40 wt %. Most preferably, the disintegrant is crospovidone in an amount of about 25 to about 35 wt % and another disintegrant (preferably croscarmellose sodium) is used in amounts of about 8 to about 25 wt %.

When used as a disintegrant, the crospovidone generally has a particle size of about 20 $\mu$M to about 250 $\mu$M, with about 50 $\mu$M to about 250 $\mu$M being preferred.

In addition to the disintegrant, the compressible tablet also preferably comprises one lubricant, one surfactant and one glidant.

For chewable tablets, the composition generally comprises about 20 to about 50 wt % of the molecular dispersion, about 78 to about 98 wt % of a bulking agent (e.g., a sugar such as xylitol), and about 0.2 to about 1 wt % of a lubricant, optionally about 0.2 to about 1 wt % of an artificial sweetener (e.g., sodium saccharin or aspartame), and optionally about 0.2 to about 1 wt % of a colorant.

A preferred composition for tablets comprises: (1) about 58.8 wt % of a molecular dispersion comprising (a) a compound of Formula I and (b) povidone, wherein the ratio of said compound to said polymer is about 1:1; (2) about 32.6 wt % of croscarmellose sodium (disintegrant); (3) or about 32.6 wt % of crospovidine (disintegrant); (4) about 0.3 wt % of magnesium stearate (lubricant); (5) about 7.4 wt % of Pluronic® F-68 (surfactant); and about 0.9 wt % of silicon dioxide (glidant). More preferably, the povidone has a molecular weight of about 29,000 to about 44,000. A preferred composition is illustrated in Examples below.

DOSING PROTOCOL FOR MONKEYS

The formulation to be tested was administered orally to male cynomolgus monkeys in a single dose (PO, single). The number of monkeys for each test is indicated by the letter "N" followed by an equal sign and a number. Thus, "(N=6)" means the formulation was administered to six monkeys. The total amount of the compound of Formula I administered was 100 or 200 mg given as one capsule or tablet containing 100 or 200 mg each. The administered dose (tablet, capsule or control suspension) was slowly washed down with 10 mL of water. Blood samples were taken at 15, 30 minutes, 1 hour, 2 hours, 4 hours, 6 hours, 8 hours, 12 hours, 24 hours, and 48 hours in heparinized syringes. Plasma for analysis was obtained by centrifugation at 4° C. Plasma samples (one per time point) were split and stored at –20° C. until assayed as described below.

The monkeys to be tested were fed two biscuits in the morning on the day of drug administration.

Monkeys that were fasted were not given any food overnight before drug administration and were fed normally after the 4-hour time point after drug administration.

BIOAVAILABILITY ASSAY

Samples of monkey plasma were collected at selected time intervals. The plasma was analyzed by a high pressure liquid chromatograph (HPLC) procedure with ultraviolet detection. AUC (area under the plasma concentration-time curve, 0–72 hours) values were calculated using standard procedures to determine the relative bioavailability of the compound in the tested formulations. The larger the AUC value, the greater the bioavailability.

A suspension of the compound of Formula I was used as a control. The control was made by suspending sufficient compound of Formula I in methyl cellulose solution to provide a dose of 30 mg/kg of body weight of monkey. The 0.4% methyl cellulose solution was made by adding 4 grams of methyl cellulose to one liter of distilled water and heating at about 80° C. with stirring for about 1½ hours.

The results of the bioavailability assay are given in terms of percent-relative bioavailability (AUC ratio) compared to amorphous suspension of Compound I in 0.4 methyl cellulose solution.

EXAMPLE 1

Preparation of Molecular Dispersion

| Composition | g/batch | % composition |
|---|---|---|
| Compound I crystalline | 7 | 25 |
| Povidone NF K29132 | 21 | 75 |
| Methylene Chloride | 1000 mL | evaporates |

Crystalline Compound I and the povidone were dissolved in methylene chloride. The solvent was evaporated under a hood, and then the residue was dried under a suitable vacuum. The residue was then reduced to fine particles by grinding. The powder was then passed through a 30 mesh screen. The powder was found to be amorphous by x-ray analysis.

EXAMPLE 2

Preparation of Molecular Dispersion

| Composition | g/batch | % composition |
| --- | --- | --- |
| Compound I crystalline | 10 | 33.3 |
| Povidone NF K29/32 | 20 | 66.6 |
| Methylene Chloride | 500 mL | evaporates |

Crystalline Compound I and the povidone were dissolved in methylene chloride. The solvent was evaporated under a hood, and then the residue was dried under a suitable vacuum. The residue was then reduced to fine particles by grinding. The powder was then passed through a 30 mesh screen. The powder was found to be amorphous by x-ray analysis.

EXAMPLE 3

Preparation of Molecular Dispersion

| Composition | g/batch | % composition |
| --- | --- | --- |
| Compound I crystalline | 5 | 50 |
| Povidone NF K29/32 | 5 | 50 |
| Methylene Chloride | 300 mL | evaporates |

Crystalline Compound I and the povidone were dissolved in methylene chloride. The solvent was evaporated under a hood, and then the residue was dried under a suitable vacuum. The residue was then reduced to fine particles by grinding. The powder was then passed through a 30 mesh screen. The powder was found to be amorphous by x-ray analysis.

EXAMPLE 4

Preparation of Molecular Dispersion

| Composition | g/batch | % composition |
| --- | --- | --- |
| Compound I crystalline | 10 | 25 |
| Povidone NF K29/32 | 30 | 75 |
| Methylene Chloride | 140 mL | evaporates |
| Methanol | 60 mL | evaporates |

Crystalline Compound I and the povidone were dissolved in a mixture of methylene chloride and methanol. The solvent was evaporated under a hood, and then the residue was dried under a suitable vacuum. The residue was then reduced to fine particles by grinding. The powder was then passed through a 30 mesh screen. The powder was found to be amorphous by x-ray analysis.

EXAMPLE 5

Preparation of Molecular Dispersion

| Composition | g/batch | % composition |
| --- | --- | --- |
| Compound I crystalline | 7.5 | 33.3 |
| Povidone NF K29/32 | 15 | 66.6 |
| Methylene Chloride | 140 mL | evaporates |
| Methanol | 60 mL | evaporates |

Crystalline Compound I and the povidone were dissolved in a mixture of methylene chloride and methanol. The solvent was evaporated under a hood, and then the residue was dried under a suitable vacuum. The residue was then reduced to fine particles by grinding. The powder was then passed through a 30 mesh screen. The powder was found to be amorphous by x-ray analysis.

EXAMPLE 6

Preparation of Molecular Dispersion

| Composition | g/batch | % composition |
| --- | --- | --- |
| Compound I crystalline | 15 | 50 |
| Povidone NF K29/32 | 15 | 50 |
| Methylene Chloride | 140 mL | evaporates |
| Methanol | 60 mL | evaporates |

Crystalline Compound I and the povidone were dissolved in a mixture of methylene chloride and methanol. The solvent was evaporated under a hood, and then the residue was dried under a suitable vacuum. The residue was then reduced to fine particles by grinding. The powder was then passed through a 30 mesh screen. The powder was found to be amorphous by x-ray analysis.

EXAMPLE 7

Preparation of Molecular Dispersion

| Composition | g/batch | % composition |
| --- | --- | --- |
| Compound I | 80 | 33.3 |
| Povidone NF K29/32 | 160 | 66.6 |
| Methylene Chloride | 5000 mL | evaporates |

Crystalline Compound I and the povidone were dissolved in methylene chloride. The solvent was removed using a double drum dryer. The residue was then reduced to fine particles by grinding. The powder was then passed through a 30 mesh screen. The powder was found to be amorphous by x-ray analysis.

EXAMPLE 8

| Preparation of Molecular Dispersion | | |
|---|---|---|
| Composition | g/batch | % composition |
| Compound I | 80 | 25 |
| Povidone NF K29/32 | 240 | 75 |
| Methylene Chloride | 5000 mL | evaporates |

Crystalline Compound I and the povidone were dissolved in methylene chloride. The solvent was removed using a suitable vacuum double drum dryer. The residue was then reduced to fine particles by grinding. The powder was then passed through a 30 mesh screen. The powder was found to be amorphous by x-ray analysis.

EXAMPLE 9

Preparation of Molecular Dispersion

The solution from Example 7 was dried using a suitable solvent spray dryer.

EXAMPLE 10

Preparation of Molecular Dispersion

The solution from Example 8 was dried using a suitable solvent spray dryer.

EXAMPLE 11

Preparation of Molecular Dispersion

The solution from Example 6 was dried using a suitable solvent spray dryer.

EXAMPLE 12

| Capsule Formulation | | |
|---|---|---|
| Composition | mg/capsule | % composition |
| Molecular Dispersion from Example 1 | 400 | 84.2 |
| Pluronic F68 NF | 25 | 5.2 |
| Croscarmellose Sodium NF | 42.5 | 8.9 |
| Silicon Dioxide NF | 5 | 1.1 |
| Magnesium Stearate NF | 2.5 | 0.6 |
| TOTAL | 475 | |
| Capsule Size | No. 0 | |

Method

The molecular dispersion of Example 1, the Pluronic, the croscarmellose sodium, and silicon dioxide were mixed in a suitable mixer for 10 minutes. A premix was formed with the magnesium stearate and an equal portion of the mixture. The premix was added to the mixture and the resulting mixture was mixed for an additional 5 minutes. The mixture was encapsulated in No. 0 hard shell gelatin capsules.

EXAMPLE 13

| Capsule Formulation | | |
|---|---|---|
| Composition | mg/capsule | % composition |
| Molecular Dispersion from Example 6 | 200 | 72.7 |
| Pluronic F68 NF | 25 | 9.1 |
| Croscarmellose Sodium NF | 42.5 | 15.5 |
| Silicon Dioxide NF | 5 | 1.8 |
| Magnesium Stearate NF | 2.5 | 0.9 |
| TOTAL | 275 | |
| Capsule Size | No. 2 | |

Method

The molecular dispersion of Example 6, the Pluronic, the croscarmellose sodium, and silicon dioxide were mixed in a suitable mixer for 10 minutes. A premix was formed with the magnesium stearate and an equal portion of the mixture. The premix was added to the mixture and the resulting mixture was mixed for an additional 5 minutes. The mixture was encapsulated in No. 2 hard shell gelatin capsules.

EXAMPLE 14

| Capsule Formulation | | |
|---|---|---|
| Composition | mg/capsule | % composition |
| Molecular Dispersion from Example 6 | 200 | 80 |
| Pluronic F68 NF | 25 | 10 |
| Croscarmellose Sodium NF | 20 | 8 |
| Silicon Dioxide NF | 3.75 | 1.5 |
| Magnesium Stearate NF | 1.25 | 0.5 |
| TOTAL | 250 | |
| Capsule Size | No. 2 | |

Method

The molecular dispersion of Example 6, the Pluronic, the croscarmellose sodium, and silicon dioxide were mixed in a suitable mixer for 10 minutes. A premix was formed with the magnesium stearate and an equal portion of the mixture. The premix was added to the mixture and the resulting mixture was mixed for an additional 5 minutes. The mixture was encapsulated in No. 2 hard shell gelatin capsules.

EXAMPLE 15

| Capsule Formulation | | |
|---|---|---|
| Composition | mg/capsule | % composition |
| Molecular Dispersion from Example 6 | 400 | 80 |
| Pluronic F68 NF | 50 | 10 |
| Croscarmellose Sodium NF | 40 | 8 |
| Silicon Dioxide NF | 7.5 | 1.5 |
| Magnesium Stearate NF | 2.5 | 0.5 |
| TOTAL | 500 | |
| Capsule Size | No. 0 | |

Method

The molecular dispersion of Example 6, the Pluronic, the croscarmellose sodium, and silicon dioxide were mixed in a suitable mixer for 10 minutes. A premix was formed with the magnesium stearate and an equal portion of the mixture. The premix was added to the mixture and the resulting mixture was mixed for an additional 5 minutes. The mixture was encapsulated in No. 0 hard shell gelatin capsules.

EXAMPLE 16

| Tablet Formulation | | |
| --- | --- | --- |
| Composition | mg/tablet | % composition |
| Molecular Dispersion from Example 4 | 400 | 66.7 |
| Pluronic F68 | 25 | 4.2 |
| Croscarmellose Sodium NF | 167.5 | 27.9 |
| Silicon Dioxide | 5 | 0.8 |
| Magnesium Stearate | 2.5 | 0.4 |
| TOTAL | 600 | |

Method

The molecular dispersion of Example 4, the Pluronic, the croscarmellose sodium, and silicon dioxide were mixed in a suitable mixer for 10 minutes. A premix was formed with the magnesium stearate and an equal portion of the mixture. The premix was added to the mixture and the resulting mixture was mixed for an additional 5 minutes. The resulting mixture was then compressed into tablets using a suitable tabletting machine.

EXAMPLE 17

| Tablet Formulation | | |
| --- | --- | --- |
| Composition | mg/tablet | % composition |
| Molecular Dispersion from Example 5 | 300 | 66.7 |
| Pluronic F68 | 25 | 5.5 |
| Crospovidone NF | 30 | 6.7 |
| Croscarmellose Sodium NF | 89 | 19.8 |
| Silicon Dioxide | 4 | 0.9 |
| Magnesium Stearate | 2 | 0.4 |
| TOTAL | 450 | |

Method

The molecular dispersion of Example 5, the Pluronic, the crospovidone and croscarmellose sodium, and silicon dioxide were mixed in a suitable mixer for 10 minutes. A premix was formed with the magnesium stearate and an equal portion of the mixture. The premix was added to the mixture and the resulting mixture was mixed for an additional 5 minutes. The resulting mixture was then compressed into tablets using a suitable tabletting machine.

EXAMPLE 18

| Tablet Formulation | | |
| --- | --- | --- |
| Composition | mg/tablet | % composition |
| Molecular Dispersion from Example 6 | 200 | 58.8 |
| Pluronic F68 | 25 | 7.4 |
| Crospovidone NF | 110.75 | 32.6 |
| Silicon Dioxide | 3 | 0.9 |
| Magnesium Stearate | 1.25 | 0.3 |
| TOTAL | 340 | |

Method

The molecular dispersion of Example 6, the Pluronic, the crospovidone, and silicon dioxide were mixed in a suitable mixer for 10 minutes. A premix was formed with the magnesium stearate and an equal portion of the mixture. The premix was added to the mixture and the resulting mixture was mixed for an additional 5 minutes. The resulting mixture was then compressed into tablets using a suitable tabletting machine.

EXAMPLE 19

| Tablet Formulation | | |
| --- | --- | --- |
| Composition | mg/tablet | % composition |
| Molecular Dispersion from Example 6 | 200 | 58.8 |
| Pluronic F68 | 25 | 7.4 |
| Croscarmellose Sodium NF | 110.75 | 32.6 |
| Silicon Dioxide | 3 | 0.9 |
| Magnesium Stearate | 1.25 | 0.3 |
| TOTAL | 340 | |

Method

The molecular dispersion of Example 6, the Pluronic, the croscarmellose sodium, and silicon dioxide were mixed in a suitable mixer for 10 minutes. A premix was formed with the magnesium stearate and an equal portion of the mixture. The premix was added to the mixture and the resulting mixture was mixed for an additional 5 minutes. The resulting mixture was then compressed into tablets using a suitable tabletting machine.

EXAMPLE 20 AND 21

| Capsule Formulation | | | |
| --- | --- | --- | --- |
| Composition | 20 mg/capsule | 21 mg/capsule | % composition |
| Molecular Dispersion from Example 9 | 100 | 400.0 | 84.2 |
| Silicon Dioxide NF[1] | 0.625 | 2.5 | 0.5 |
| Magnesium Stearate NF[2] | 0.125 | 0.5 | 0.1 |
| Croscarmellose Sodium NF | 11.000 | 44.0 | 9.3 |
| Pluronic F68 NF | 6.250 | 25.0 | 5.3 |
| Silicon Dioxide NF[3] | 0.625 | 2.5 | 0.5 |
| Magnesium Stearate NF[4] | 0.125 | 0.5 | 0.1 |

-continued

Capsule Formulation

| Composition | 20 mg/capsule | 21 mg/capsule | % composition |
|---|---|---|---|
| TOTAL | 118.750 | 475.00 | |
| Capsule Size | No. 4 | No. 0 | |

Method

The molecular dispersion from example 9, silicon dioxide [1] and magnesium stearate [2] mixed in a suitable mixer for 10 minutes. The mixture is compacted using a suitable roller compacted and milled using a suitable mill fitted with 30 mesh screen. Croscarmellose sodium, Pluronic F68 and silicon dioxide [3] are added to the milled mixture and mixed further for 10 minutes. A premix was made with the magnesium stearate [4] and an equal portion of the mixture. The premix was added to the remainder of the mixture and mixed for 5 minutes. The mixture was encapsulated in hard shell gelatin capsule.

EXAMPLE 22 AND 23

Capsule Formulation

| Composition | 22 mg/capsule | 23 mg/capsule | % composition |
|---|---|---|---|
| Molecular Dispersion from Example 11 | 400 | 200.0 | 80.0 |
| Silicon Dioxide NF[1] | 3.75 | 1.875 | 0.75 |
| Magnesium Stearate NF[2] | 1.25 | 0.625 | 0.25 |
| Croscarmellose Sodium NF | 40.00 | 20.00 | 8.0 |
| Pluronic F68 NF | 50.00 | 25.00 | 10 |
| Silicon Dioxide NF[3] | 3.75 | 1.875 | 0.75 |
| Magnesium Stearate[4] | 1.25 | 0.625 | 0.25 |
| TOTAL | 500.00 | 250.00 | |
| Capsule Size | No. 0 | No. 2 | |

Method

The molecular dispersion from example 11, silicon dioxide[1] and magnesium stearate[2] mixed in a suitable mixer for 10 minutes. The mixture is compacted using a suitable roller compactor and milled using a suitable mill fitted with 30 mesh screen. Croscarmellose sodium, Pluronic F68 and silicon dioxide[3] are added to the milled mixture and mixed further for 10 minutes. A premix was made with the magnesium stearate[4] and an equal portion of the mixture. The premix was added to the remainder of the mixture and mixed for 5 minutes. The mixture was encapsulated in hard shell gelatin capsule.

EXAMPLE 24 AND 25

Chewable Tablet

| Composition | 24 mg/tablet | 25 mg/tablet | % composition |
|---|---|---|---|
| Molecular Dispersion from Example 11 | 400 | 800 | 40 |
| Xylitol | 585 | 1170 | 58.5 |
| Cherry flavor Concentrate (spray dried) | 5 | 10 | 0.5 |
| FD & C Yellow No. 6 lake | 5 | 10 | 0.5 |
| Magnesium Stearate | 5 | 10 | 0.5 |
| TOTAL | 1000 | 2000 | |

Method

Mix the molecular dispersion from example 11, xylitol in a suitable mixer for 10 minutes. Make a premix of flavor, color and a portion of the mixture, pass through 30 mesh screen. Add the premix to the remainder of the mixture and mix for an additional 10 minutes. Make a premix of the portion of the above mixture and magnesium stearate. Pass through 30 mesh screen. Add the premix to the balance of the mixture and mix for 5 minutes. The resulting mixture compressed into tablets using a tablet machine.

EXAMPLE 26

Preparation of Molecular Dispersion

| Composition | g/batch | % composition |
|---|---|---|
| Compound I | 8.0 | 25 |
| Polyethylene Glycol 8000 NF | 24.0 | 75 |
| Methylene Chloride | 5000 mL | |

Crystalline compound I and polyethylene glycol 8000 were dissolved in methylene chloride and the solvent removed under the hood and then the residue was further dried under a suitable vacuum. The residue was then reduced to fine particles by grinding. The powder was then passed through a 30 mesh screen. The powder was found to be amorphous by x-ray analysis.

EXAMPLE 27

Capsule Formulation

| Composition | g/batch | % composition |
|---|---|---|
| Molecular Dispersion from Example 26 | 400 | 84.2 |
| Pluronic F68 NF | 25 | 5.2 |
| Croscarmellose Sodium NF | 42.5 | 8.9 |
| Silicon Dioxide NF | 5 | 1.1 |
| Magnesium Stearate NF | 2.5 | 0.6 |
| Total | 475.5 | |
| Capsule Size | No. 0 | |

Method

The molecular dispersion from example 26, the Pluronic F68, the croscarmellose sodium and silicon dioxide were mixed in a suitable mixer for 10 minutes. A premix was formed with the magnesium stearate and an equal portion of the mixture. The premix was added to the mixture and the resulting mixture was mixed for an additional 5 minutes. The mixture was encapsulated in No. 0 hard shell gelatin capsule.

The bioavailability of the compound of Formula I was extremely poor and development of a solid dosage form by use of conventional excipients was unsuccessful. Formulations containing the molecular dispersions of this invention were prepared and compared to a control composition consisting of a suspension of the compound of Formula I.

The relative bioavailability of suspensions of the crystalline form of the compound I were prepared and compared to suspension of the amorphous form of compound I in both fasted and fed male cynomolgus monkeys.

The relative bioavailability of suspensions containing crystalline compound I was 1.3% of the AUC and 2.7% of the Cmax of the suspensions containing the amorphous form of compound I. In fed monkeys, the relative bioavailability of suspensions of the crystalline compound I was 3.6% of the AUC and 5.2% of the C max of suspensions containing the amorphous form of compound I.

The relative bioavailability of formulations containing molecular dispersions of this invention were determined in fed monkeys using in comparison to suspensions containing amorphous compound I.

| Formulation Example | Bioavailability % |
|---|---|
| No. 12 | 82 |
| No. 13 | 70 |
| No. 15 | 87 |
| No. 16 | 65 |
| No. 17 | 59 |
| No. 18 | 58 |
| No. 19 | 58 |

We claim:

1. The pharmaceutical composition in a solid dosage form for oral consumption, comprising a compound having the formula I:

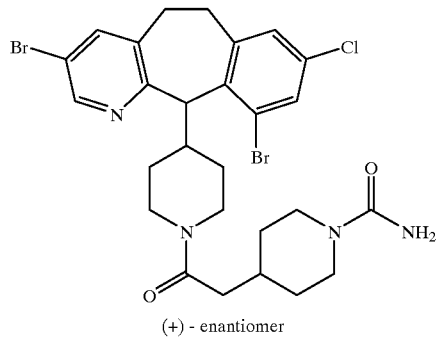

(+) - enantiomer molecularly dispersed in a polymer matrix consisting essentially of polyvinylpyrrolidone, wherein the compound is present in a proportion of form about 15 to 60% by weight, based on the total weight of the pharmaceutical composition, a ratio of the compound to the polymer is from about 1:0.5 to about 1:4, and the solid form pharmaceutical composition has an enhanced bioavailability when orally consumed compared to orally consumed solid form pharmaceutical compositions that comprise the compound having the formula I where it is not molecularly dispersed in the polymer matrix.

2. The pharmaceutical composition of claim 1 wherein the ratio of said compound to polyvinylpyrrolidone is about 1:1 to about 1:3.

3. The pharmaceutical composition of claim 1 wherein the ratio of said compound to polyvinylpyrrolidone is about 1:1.

* * * * *